United States Patent
Smith et al.

(10) Patent No.: US 6,718,982 B2
(45) Date of Patent: Apr. 13, 2004

(54) FACE MASK INCORPORATING RESPIRATORY FLOW SENSOR

(76) Inventors: Mark A. Smith, 4414 W. Liberty Rd., Ann Arbor, MI (US) 48103; Rex T. Fasching, 1396 - 16th Ave. N.W., New Brighton, MN (US) 55112; C. Peter Howard, 26 Leewood Dr., Humboldt, TN (US) 38343

(*) Notice: Subject to any disclaimer, the term of this patent is extended or adjusted under 35 U.S.C. 154(b) by 279 days.

(21) Appl. No.: 09/850,334

(22) Filed: May 7, 2001

(65) Prior Publication Data

US 2002/0162556 A1 Nov. 7, 2002

(51) Int. Cl.⁷ .............................................. A61M 16/00
(52) U.S. Cl. ............................. 128/207.12; 128/206.21
(58) Field of Search ........................... 128/857, 206.25, 128/206.19, 207.12, 206.21

(56) References Cited

U.S. PATENT DOCUMENTS

| | | | |
|---|---|---|---|
| 4,802,473 A | * 2/1989 | Hubbard et al. | 128/206.19 |
| 5,038,773 A | 8/1991 | Norlien et al. | 128/205.23 |
| D334,633 S | 4/1993 | Rudolph | D29/7 |
| 5,265,595 A | 11/1993 | Rudolph | 128/204.18 |
| 5,363,857 A | 11/1994 | Howard | 128/718 |
| 5,538,000 A | 7/1996 | Rudolph | 128/205.25 |
| 5,538,013 A | * 7/1996 | Brannon | 128/857 |
| D385,960 S | 11/1997 | Rudolph | D24/110.4 |
| 5,705,735 A | 1/1998 | Acorn | 73/23.3 |
| 5,918,598 A | * 7/1999 | Belfer et al. | 128/206.25 |
| 6,082,360 A | * 7/2000 | Rudolph et al. | 128/206.25 |

OTHER PUBLICATIONS

Respro Filter Masks, Mike P. Stroke, webmaster@immuneweb.org, Feb. 1996.

* cited by examiner

Primary Examiner—Henry Bennett
Assistant Examiner—Sabrina Dagostino
(74) Attorney, Agent, or Firm—Thomas J. Nikolai; Nikolai & Mersereau, P.A.

(57) ABSTRACT

A respiratory monitor apparatus comprises, in combination, a flexible mask fabricated from a stretchable fabric, such as spandex, that is designed to support a pneumotach flow measuring instrument in a way that does not require the instrument to be placed in the wearer's mouth, yet still remaining in fluid communication with the wearer's mouth and with little or no dead-space or leakage between the mask member and the wearer's face.

17 Claims, 5 Drawing Sheets

FACE MASK INCORPORATING RESPIRATORY FLOW SENSOR

BACKGROUND OF THE INVENTION

I. Field of the Invention

This invention relates generally to respiration monitoring apparatus, and more particularly to a face mask mounted pneumotachograph that obviates the need for the wearer to insert the pneumotachograph in his/her mouth as inspiratory and expiratory gas flows are being measured.

II. Discussion of the Prior Art

In the Howard U.S. Pat. No. 5,363,857, assigned to AeroSport, Inc., there is described a metabolic rate analyzer that measures flow, $O_2$ consumption and $CO_2$ production and provides a readout of a test subject's respiratory performance obtained during the course of an exercise regimen. In the system described, the test subject is made to breath in and out through a mouthpiece as differing levels of work are performed on a treadmill or stationary bicycle.

The Norlien et al. U.S. Pat. No. 5,038,773, also assigned to applicants' assignee, describes a respiratory gas flow measuring and indicating system that incorporates a tubular, molded plastic, open-ended structure in the lumen of which is provided a pair of molded ribs which intersect to form a cross. The ribs are also tubular and each includes a series of minute apertures and opposed sides thereof which act as pitot tubes. As is described in the '773 patent, the invention of that patent offers significant advantages over known pneumotachograph devices. For example, because the mouthpiece of the flow meter system of the '773 patent has a very low dead space, gas analyzers incorporated in the system are not adversely affected by the rebreathing of previously expired, $CO_2$ rich air. However, with a mouthpiece that is designed to be held in the mouth between the lips of the subject, swallowing becomes somewhat more difficult and there is a tendency to gather saliva in the mouth, especially in subject's undergoing heavy exercise. Saliva can collect on the cruciform ribs of the pneumotachograph and occlude the apertures comprising the pitot tube structure, thus resulting in inaccurate gas flow measurements. Thus, it would be advantageous to have a respiratory gas flow measurement sensor that need not be inserted in the test subject's mouth. The Rudolph U.S. Pat. No. 5,265,595, assigned to Hans Rudolph, Inc., describes a face mask structure designed to support a pneumotachograph in close proximity to, but not in, the test subject's mouth. The particular mask design reflected in the '595 patent purports to provide a low dead space between the subject's face and the portion of the mask that is designed to encircle and cover the subject's mouth.

As is set out in a subsequent Rudolph et al. U.S. Pat. No. 6,082,360, the device described in the Rudolph '595 patent suffers from a serious defect, namely, the mask of the '595 patent leaks air around the periphery of the mask when being worn by a user which allows escape of expired gases from the mask or drawing outside air into the mask other than through the pneumotachograph. The solution set forth in the Rudolph '360 patent is to apply a sticky, moist hydrogel seal between the patient's skin and the mask in an effort to cure the leakage problem. It has been reported that many subjects consider the application and subsequent removal of the sticky, moist seal to be somewhat unpleasant.

A need, therefore, exists for a face mask that (1) incorporates a respiratory flow sensor that substantially eliminates any dead space between the wearer's face and the flow sensor and which also seals tightly against the face of the wearer to prevent air leakage; (2) is sufficiently low cost so as to allow single patient use in a clinical setting and yet be launderable in those applications where the respiratory measurements are being made in a health club setting; and (3) that reduces anxiety and stress by being comfortable and effective allowing normal work to continue.

SUMMARY OF THE INVENTION

The foregoing advantages are achieved by providing a respiratory monitor apparatus that has a mask adapted to be secured to the face of a person so as to enclose the nose and mouth where the mask is formed from a soft, conformable, gas-impermeable elastic fabric allowing it to conform to the person's face with substantially zero air space therebetween. The elastic fabric has at least one aperture of a predetermined size and shape extending through its thickness dimension incorporating a soft rubber grommet. A respiratory flow sensor is mounted within the grommet and is of a size and shape to exhibit a zero clearance fit with a portion of the mask defining the aperture.

The elastic fabric is preferably spandex, formed from woven Lycra® fibers and to provide more rigid support for the flow sensor, the spandex fabric may be laminated with neoprene sponge rubber of a predetermined thickness.

DESCRIPTION OF THE DRAWINGS

The foregoing features, objects and advantages will become apparent to those skilled in the art from the following detailed description of the preferred embodiment, especially when considered in conjunction with the accompanying drawings in which.

DESCRIPTION OF THE PREFERRED EMBODIMENT

Figure 1:
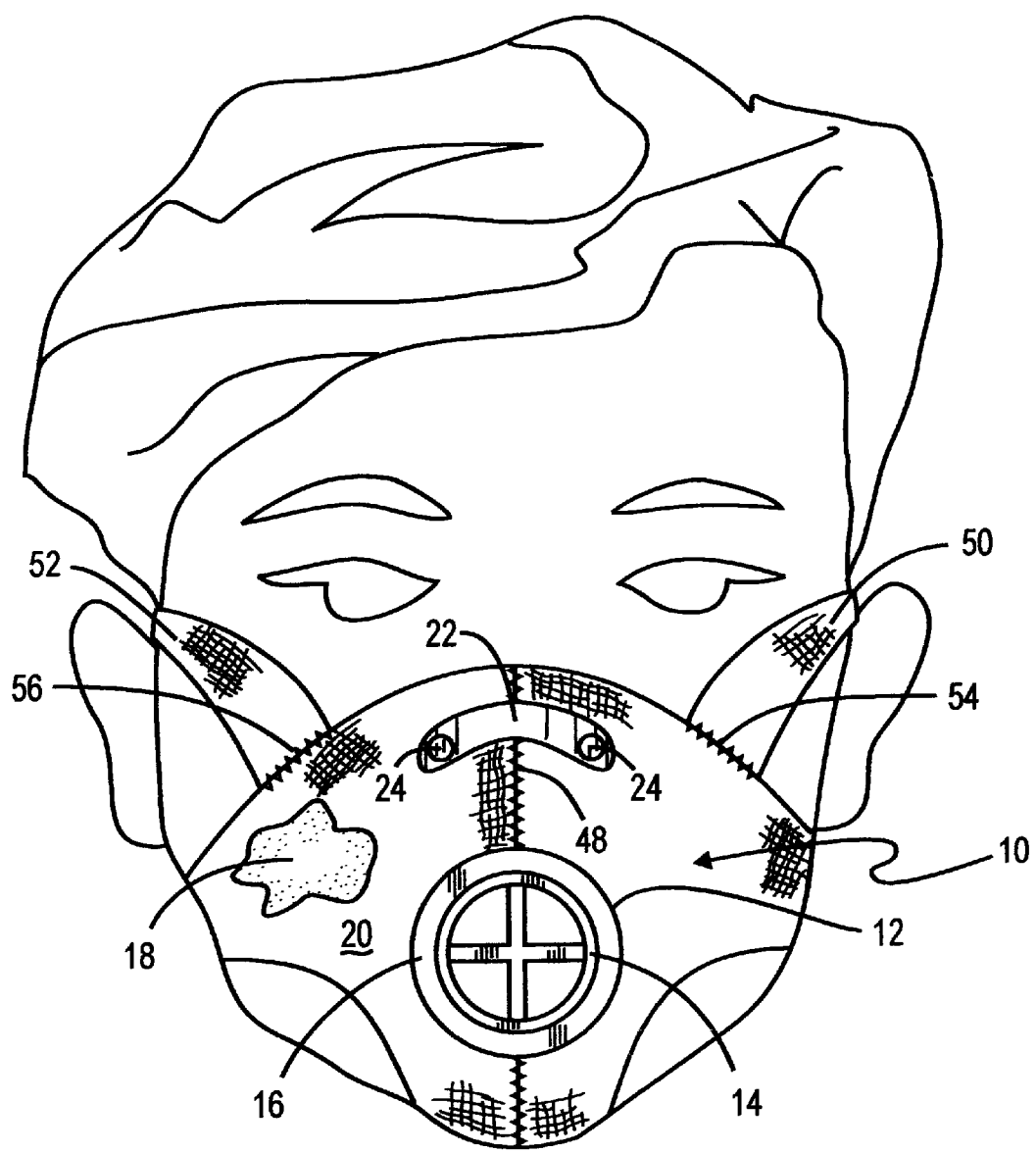
FIG. 1 is a frontal view of a respiratory monitor mask disposed on a subject's face.

With reference first to FIGS. 1–4 of the drawings, the respiratory monitor apparatus of the present invention comprises a mask 10 that is adapted to be worn on the face of a subject in covering relating to the subject's nose and mouth. Formed through the thickness dimension of the mask is an aperture, as at 12, through which a tubular pneumotachograph (pneumotach) 14 projects. The aperture is positioned so as to align with the subject's mouth when the mask is being worn. To provide a more rigid support for the pneumotach 14, it has been found expedient to utilize a soft rubber grommet 16 that is stretched to receive the outside cylindrical surface of the pneumotach 14 through the center opening thereof and whose outside diameter forms a zero clearance fit with the aperture 12 formed in the mask.

The mask 10 is preferably formed from Lycra® fibers woven as a spandex fabric, allowing it to stretch and conform closely to the contour of the wearer's face with very little, if any, dead space between the inside surface of the mask 10 and the subject's face. To render the mask gas impermeable, it has been found convenient to laminate a layer of neoprene foam rubber 18 between outer and inner spandex fabric layers as at 20. Neoprene foam sheets laminated on both sides with highly stretchable spandex fabric is available in a variety of thicknesses from National Webbing Products Co. of Garden City Park, N.Y., in various colors. In fabricating the mask of the present invention, we have found thicknesses in a range of from 1–3 mm to be ideal.

To make the mask better conform to the bridge of the wearer's nose, it has been found convenient to provide a soft malleable metal clip, as at 22, that is riveted to the mask by rivets 24. The clip 22 may readily be pinched and thereby bent over the bridge of the nose to further aid in reducing dead space between the mask and the wearer's face.

In the embodiment of FIG. 1, the pneumotach 14 is preferably of the type described in the aforereferenced Norlien et al. '773 patent and which is available from Medical Graphics Corporation of St. Paul, Minn., as its Part No. 541115 pneumotach mouthpiece.

Figure 2:
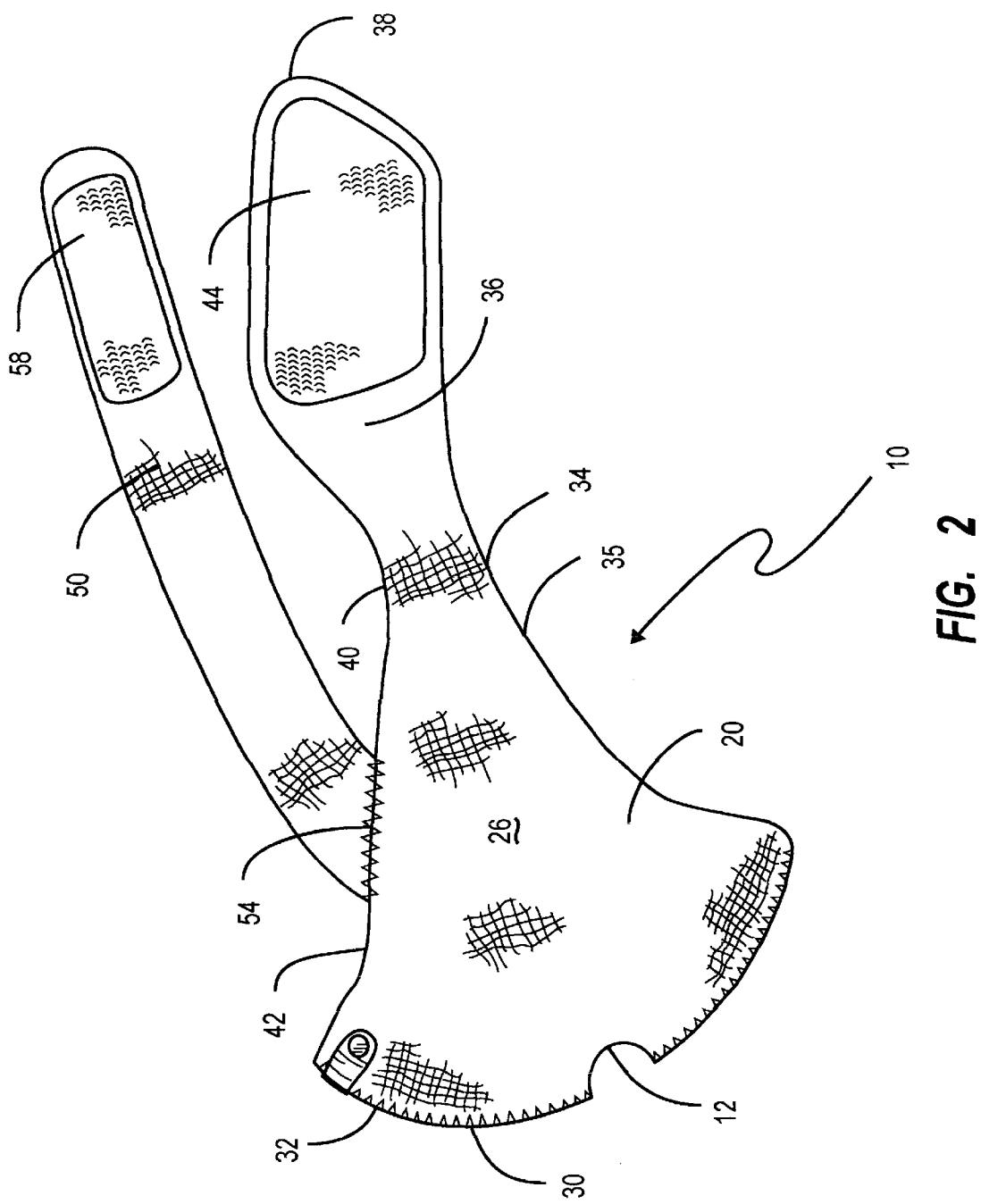
FIG. 2 is a side elevation of the face mask portion of the respiratory monitor apparatus of FIG. 1.
Figure 3:
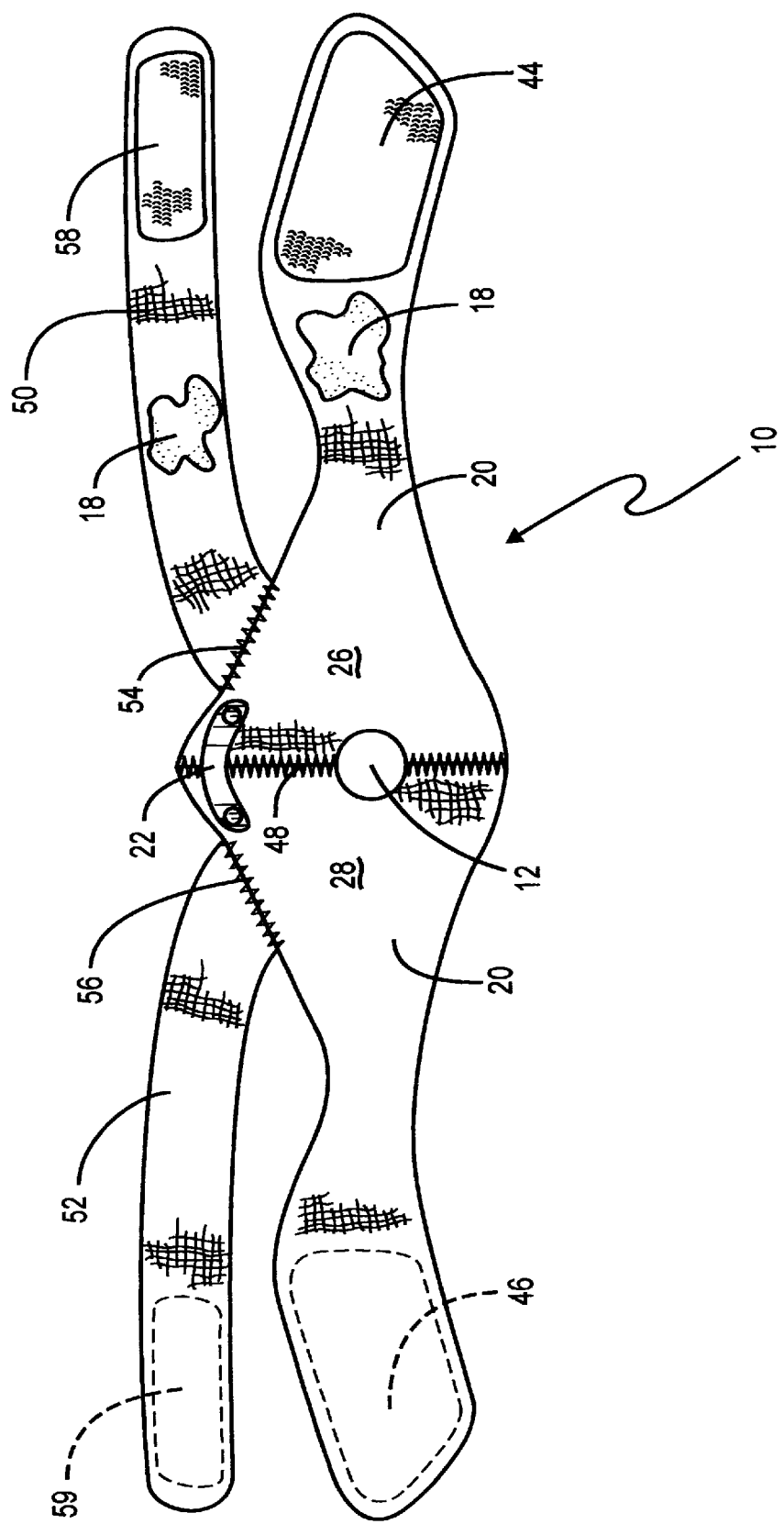
FIG. 3 is a frontal view of the face mask of FIG. 2.
Figure 4:
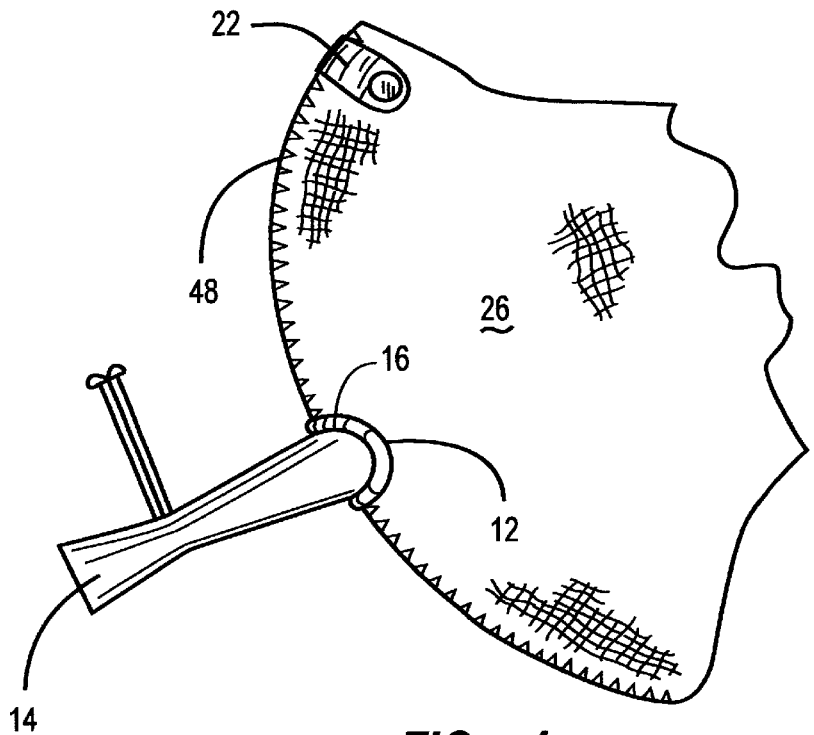
FIG. 4 is a partial side view of the mask of FIG. 1 with a respiratory flow sensor in place.

Turning next to FIGS. 2 and 3, the mask 10 is seen to comprise first and second mask segments 26 and 28, each formed as a lamination of outer layers of spandex fabric 20 and an inner layer of synthetic foam rubber 18. Each of the segments 26 and 28 is cut in a pattern to define a convex curve 30 of a predetermined radius of curvature at a first end 32 thereof, a concave curve 34 along a lower edge 35 thereof that joins the convex curve 30 to a generally trapezoidal shaped area 36 proximate a second end 38 thereof. The pattern further includes another concave curve 40 along an upper edge 42 that joins the trapezoidal shape area 36 to the convex curve 30. The mask segments 26 and 28 are secured together, preferably by stitching, along their respective convex curved first ends 32, thus forming symmetrical first and second mask halves.

Velcro® hook and loop fastening pads 44 and 46 (FIG. 3) are sewn, glued or otherwise affixed in the generally trapezoidal shaped areas 36 of the two joined mask segments. The hook and loop fastening pads formed in the trapezoidal areas of the first and second mask segments are adapted to be joined behind the head of the wearer and when so joined, function to stretch and conform predetermined portions of the first and second mask segments to the face of the wearer with the stitched seam 48 being generally aligned with the mid-line of the wearer's face.

It has also been found convenient to provide additional narrow straps 50 and 52, each of a predetermined length and each attached at one end 54 and 56 to the upper edges of the mask segments 26 and 28 by sewing. Suitable fasteners, preferably of the Velcro® hook and loop type are affixed to the straps 50 and 52 proximate the second end thereof so as to allow joining of the second ends of the straps 50 and 52 to one another behind the wearer's head. The straps 50 and 52, when so fastened, aid in stretching the elastic material of the mask segments 26 and 28 SO that they better conform to the contours of the wearer's face.

Figure 5:
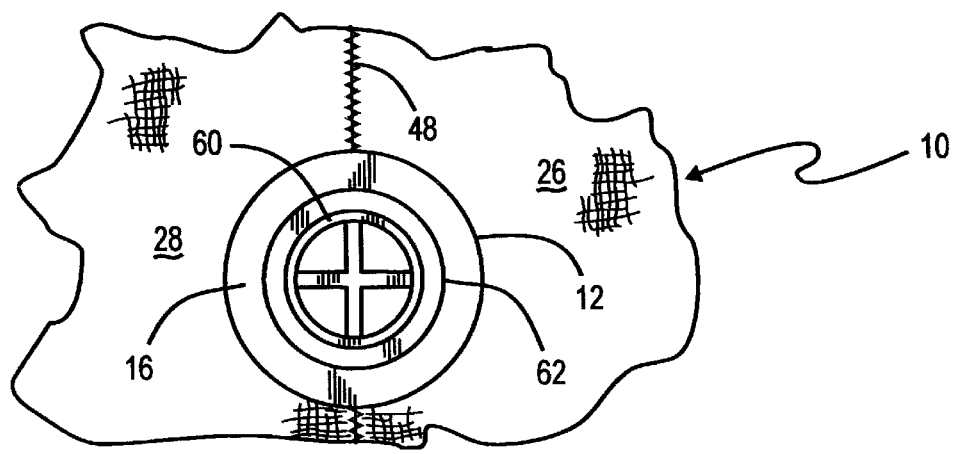
FIG. 5 is a partial front view of the mask of FIG. 1 but with a miniaturized flow sensor.

FIG. 5 is a partial frontal view of the mask 10 and showing how the smaller diameter pneumotach 60 of the type described in U.S. Pat. No. 5,705,735 to Acorn can be used with the same mask illustrated in FIGS. 2 and 3 by employing an adapter ring 62 between the inside diameter of the annular grommet 12 and the outside diameter of the low dynamic flow pneumotach 60. The adapter ring 62 is preferably fabricated from a suitable medical-grade, rigid plastic and its inner diameter is of a size to receive the pneumotach 60 therethrough with a slight friction fit sufficient to hold the pneumotach in place and to block the flow of air along the outside of the tubular barrel of the pneumotach 60. The outside diameter of the annular adapter ring 62 is slightly greater than the I.D. of the grommet 12 so that the rubber grommet 12 needs to be stretched slightly to fit over the O.D. of the adapter ring 62. By using the adapter ring 62, the same mask structure can be used with either the Medical Graphics Corporation Part No. 541115 pneumotach or its Part No. 436005 pneumotach.

Figure 6:
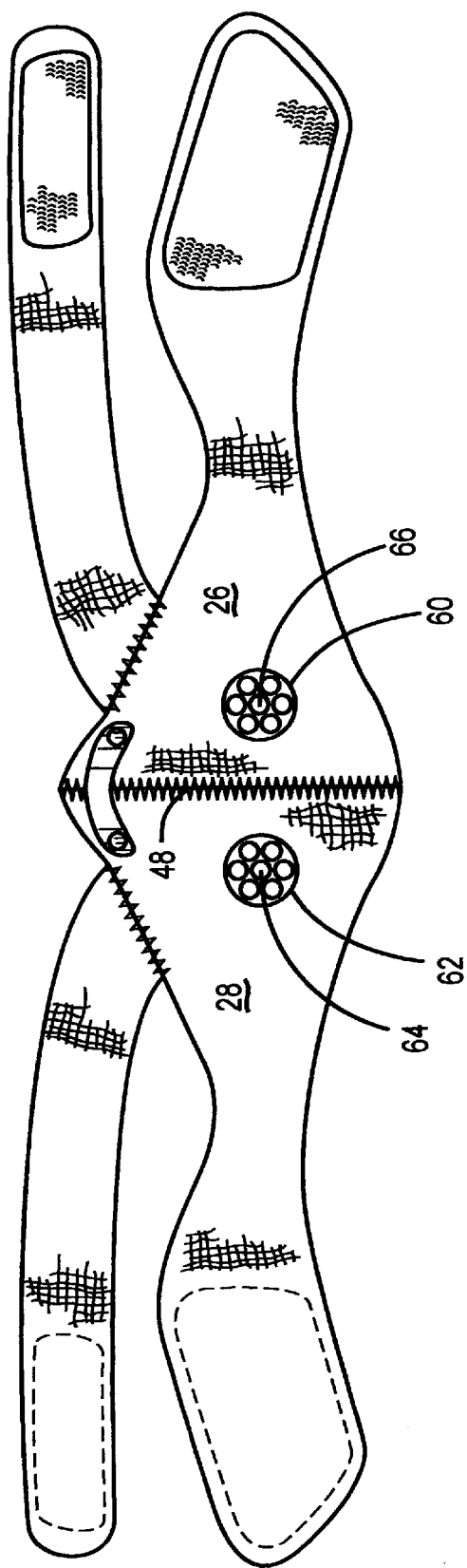
FIG. 6 is an alternative embodiment of the respiratory monitor apparatus incorporating plural, parallel-plate flow sensors.

Turning next to FIG. 6, there is shown a modified version of the mask illustrated in FIG. 3 allowing high flow, low dynamic range parallel plate style pneumotachs to be utilized. In physical fitness testing, a measure of oxygen consumption ($VO_2$) is of paramount interest. In practice, $VO_2$ is most often estimated using heart rate information and workload measured during the course of an exercise test on a treadmill or cycle ergometer. While this approach may provide a reasonable estimate of oxygen consumption for many subjects, there are still many persons for whom this predicted oxygen consumption is inaccurate. AeroSport, Inc., a subsidiary of Medical Graphics Corporation, has developed a small, lightweight metabolic analyzer that can be readily worn by a person during an exercise regimen and which receives flow information on a breath-by-breath basis from a mask-mounted pneumotach. Because, during exercise, much higher flow rates are experienced than when a subject is resting, a low dynamic range, parallel-plate pneumotachs may be employed. The mask of FIG. 6 is identical in all respects to the previously described embodiment except that a pair of apertures 60 and 62 are formed through the thickness dimension of the mask segments and are symmetrically disposed on either side of the stitched seam 48 between the mask segments 26 and 28. The apertures are generally aligned with a subject's nares. The parallel plate pneumotach may be of a type available from Medical Graphics Corporation and, as such, each comprises a pair of apertured plates, only one of which is viewable in the drawing of FIG. 6. Incoming air during inspiration and respiratory gases exhaled during expiration pass through the multiple apertures in the parallel plates comprising the pneumotachs 64 and 66 and, in doing so, create a pressure drop whose magnitude is proportional to flow. Because the parallel plate pneumotachs are relatively thin, they can be supported directly within the apertures 60 and 62 in the mask without requiring the additional support provided by the grommet 16 as in the embodiments of FIGS. 1 and 5.

It can be seen, then, that there is provided by the present invention an improved mask arrangement adapted to support a variety of pneumotach type flow monitoring devices and which can be comfortably worn by a subject undergoing exercise to provide respiratory performance information of improved accuracy because of the absence of dead spaces between the mask and the wearer's face as well as the absence of leakage paths. The mask is relatively inexpensive to manufacture and can be treated as a single use device in a clinical situation or can be laundered for use by different patients at different times in a sports/training facility.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A respiratory monitor apparatus comprising:
   (a) a mask adapted to be secured to the face of a person so as to enclose the nose and mouth of that person, the mask being formed of a gas impermeable elastic fabric that is made to conform to the person's face with substantially zero dead air space therebetween when worn, the elastic fabric having at least one aperture of a predetermined size and shape therethrough that is generally aligned with the person's mouth when the mask is in place on the person's face;
   (b) a toroidal rubber grommet fitting tightly within the aperture; and
   (c) a respiratory flow sensor having a tubular body extending through a central opening of the toroidal rubber grommet in a sealed relationship.

2. A respiratory monitor apparatus comprising:
   (a) a mask adapted to be secured to the face of a person so as to enclose the nose and the mouth of that person, the mask being formed of a gas impermeable elastic fabric that is made to conform to the person's face with substantially zero dead air space therebetween when worn, the elastic fabric having first and second apertures, each being aligned with a nare of the person when the mask is in place on the person's face, said first and second apertures each supporting and sealed to a respiratory flow sensor.

3. The respiratory monitor apparatus of claim 1 wherein the fabric comprises woven Lycra® fibers.

4. The respiratory monitor apparatus of claim 1 wherein the fabric is spandex.

5. The respiratory monitor apparatus of claim 1 wherein the fabric is laminated with sponge neoprene rubber.

6. The respiratory monitor apparatus of claim 1 and further including a deformable metal strip affixed to an exterior surface of said mask so as to overlay the bridge of a person's nose when the mask is in place on the person's face, the metal strip being readily bendable and non-resilient.

7. The respiratory monitor apparatus of claim 1 and further including:
   (a) an adapter ring surrounding and sealed to the tubular body of the respiratory flow sensor; and
   (b) the toroidal rubber grommet surrounding the adapter ring and fitting tightly within the aperture.

8. The respiratory monitor apparatus as in any one of claims 1, 3–6 and 7 wherein the mask includes at least one pair of straps for encircling the person's head, the pair of straps including hook and loop fastener material thereon for releasably joining the pair of straps together.

9. The respiratory monitor apparatus of claim 1 wherein the mask includes the at least one and a further aperture, each being aligned with a nasal opening when the mask is in place on the person's face, the at least one and the further aperture supporting and sealed to a respiratory flow sensor.

10. The respiratory monitor apparatus of claim 2 wherein the fabric is spandex.

11. The respiratory monitor apparatus of claim 2 wherein the fabric is laminated with sponge neoprene rubber.

12. The respiratory monitor apparatus of claim 2 and further including a deformable metal strip affixed to an exterior surface of said mask so as to overlay the bridge of a person's nose when the mask is in place on the person's face, the metal strip being readily bendable and non-resilient.

13. The respiratory monitor apparatus as in any one of claims 2 and 11–12 wherein the mask includes at least one pair of straps for encircling the person's head, the pair of straps including hook and loop fastener material thereon for releasably joining the pair of straps together.

14. The respiratory monitor apparatus of claim 11 wherein the fabric has a thickness in a range of from about 1 mil to about 3 mils.

15. The respiratory monitor apparatus of either claim 1 or 2 wherein the mask comprises:
   (a) first and second mask segments formed as a lamination of outer layers of spandex fabric and an inner layer of synthetic foam rubber, each segment cut in a pattern to define a convex curve of a predetermined radius of curvature at a first end thereof, a concave curve along a lower edge thereof joining the convex curve to a generally trapezoidal shaped area at a second end thereof and with a concave curve along an upper edge thereof joining the trapezoidal shaped area to the convex curve, the first and second mask segments being stitched together along their respective convex curved first ends; and
   (b) hook and loop fastening pads affixed to the generally trapezoidal shaped areas of the first and second mask segments and which, when joined together are adapted stretch and conform predetermined portions of the first and second mask segments to the face of the said person with the stitched together first ends aligned with a midline of the person's face.

16. The respiratory monitor apparatus of claim 15 and further including:
   (a) first and second straps of a predetermined length, the straps being attached at one end, respectively, to the upper edges of the first and second mask segments; and
   (b) hook and loop fastener pads affixed to the first and second straps proximate a second end to allow joining of the second ends of the first and second straps to one another.

17. The respiratory monitor apparatus of claim 16 wherein the at least one aperture is centered about a junction line where the convex curved first ends of the first and second mask segments are stitched together.

* * * * *